(12) United States Patent
Okumura (10) Patent No.: US 8,780,349 B2
(45) Date of Patent: Jul. 15, 2014

(54) COLOR MEASUREMENT APPARATUS AND COLOR MEASUREMENT METHOD

(71) Applicant: Yoshio Okumura, Suwa (JP)

(72) Inventor: Yoshio Okumura, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/745,498

(22) Filed: Jan. 18, 2013

(65) Prior Publication Data

US 2013/0188186 A1    Jul. 25, 2013

(30) Foreign Application Priority Data

Jan. 20, 2012   (JP) ................................. 2012-010232

(51) Int. Cl.
```
G01J 3/46       (2006.01)
G01J 3/02       (2006.01)
G01N 21/57      (2006.01)
G01J 3/50       (2006.01)
```

(52) U.S. Cl.
CPC .... *G01J 3/02* (2013.01); *G01J 3/46* (2013.01); *G01N 21/57* (2013.01); *G01J 3/504* (2013.01); *G01J 3/0278* (2013.01)
USPC ....................................................... 356/402

(58) Field of Classification Search
CPC ............. G01J 3/02; G01J 3/46; G01J 3/0278; G01J 3/504; G01N 21/57
USPC ............................................................ 356/402
See application file for complete search history.

(56) References Cited

U.S. PATENT DOCUMENTS

| | | | |
|---|---|---|---|
| 4,956,223 A * | 9/1990 | Arai et al. .................. 428/32.33 |
| 7,605,943 B2 | 10/2009 | Berns et al. | |
| 7,652,789 B2 | 1/2010 | Berns et al. | |
| 7,706,604 B2 | 4/2010 | Berns et al. | |
| 2007/0018906 A1* | 1/2007 | Visnovsky et al. ............ 345/1.1 |
| 2007/0182961 A1* | 8/2007 | Chadha et al. ................ 356/328 |
| 2008/0129991 A1* | 6/2008 | Bakker et al. ................. 356/301 |
| 2008/0245979 A1* | 10/2008 | Banton et al. .............. 250/559.4 |
| 2009/0284772 A1* | 11/2009 | Sai et al. ........................ 358/1.9 |
| 2010/0128263 A1* | 5/2010 | Kobayashi et al. ........... 356/300 |
| 2010/0283989 A1* | 11/2010 | Sesko ........................... 356/4.04 |

FOREIGN PATENT DOCUMENTS

| | | |
|---|---|---|
| JP | 2007-511161 A | 4/2007 |
| JP | 2007-511175 A | 4/2007 |
| JP | 2007-516663 A | 6/2007 |
| JP | 4388554 B | 12/2009 |

* cited by examiner

*Primary Examiner* — Tarifur Chowdhury
*Assistant Examiner* — Sunghee Y Gray
(74) *Attorney, Agent, or Firm* — DLA Piper LLP (US)

(57) ABSTRACT

A color measurement apparatus that performs color measurement on a printout includes a measurement unit that can perform color measurement on a target by changing a light-receiving angle, and a controller that causes the measurement unit to perform color measurement at the light-receiving angle corresponding to an index value representing unique luster of the printout.

5 Claims, 12 Drawing Sheets

FIG. 9B $$R(\lambda, \theta, i) = \underbrace{Rc(\lambda, ic)} \cdot \underbrace{Rm(\lambda, \theta, im)} / \underbrace{Rw(\lambda)}$$

|  | DIFFUSE REFLECTANCE OF INK AMOUNT SET OF COLOR INKS | MULTI-ANGLE SPECTRAL REFLECTANCE OF SINGLE METALLIC COLOR | DIFFUSE REFLECTANCE OF PRINTING MEDIUM |
|---|---|---|---|
| ACTUAL MEASUREMENT | MEASURE DIFFUSE REFLECTANCE OF COLOR PATCHES OF COLOR INKS OF PREDETERMINED NUMBER OF INK AMOUNT SETS | MEASURE MULTI-ANGLE SPECTRAL REFLECTANCE OF METALLIC PATCHES OF METALLIC INK OF SEVERAL TONES AT RESPECTIVE INK AMOUNTS | MEASURE DIFFUSE REFLECTANCE OF PRINTING MEDIUM |
| PREDICTION | PREDICT DIFFUSE REFLECTANCE OF ANY INK AMOUNT SET OF COLOR INKS USING CYNSN MODEL | PREDICT MULTI-ANGLE SPECTRAL REFLECTANCE OF ANY AMOUNT OF METALLIC INK BY INTERPOLATION |  |

· # COLOR MEASUREMENT APPARATUS AND COLOR MEASUREMENT METHOD

CROSS-REFERENCE TO RELATED APPLICATIONS

The entire disclosure of Japanese Patent Application No. 2012-10232, filed Jan. 20, 2012 is expressly incorporated by reference herein.

BACKGROUND

1. Technical Field

The present invention relates to ink that creates unique luster.

2. Related Art

In the related art, printing apparatuses produce printouts by recording inks on media such as sheets. Color values of the printouts produced using inks of related art containing pigments and the like do not greatly change in accordance with observation angle. Accordingly, the colorimetric values at a standard observation angle are used as those of the printouts and various types of processing are performed on the basis of the values. For example, refer to JP-T-2007-511175, Japanese Patent No. 4388554, and JP-T-2007-516663.

Printing apparatuses have been provided that use inks causing printouts to have unique luster such as metallic luster. Such inks contain a metal such as aluminum and the color values and reflection intensity of the inks change in accordance with the observation angle. For example, the color values of a printout observed at a certain observation angle differ from those of the printout observed at another observation angle. The difference, thus, may create a problem in the various types of processing.

SUMMARY

An advantage of some aspects of the invention is that an optimum way to observe colors on a printout having unique luster is automatically specified.

A method of manufacturing a printing apparatus that selects inks to be output using a profile in which input color data and amounts of inks including an ink creating unique luster correspond to each other according to a first aspect of the invention includes a first process in which an observation angle of the inks is set so as to correspond to an index value representing the unique luster of a printout, a second process in which the profile corresponding to the index value is created by associating color values of the amounts of the inks corresponding to the set observation angle with the input color data, and a third process in which the produced profile is recorded in a recording unit of the printing apparatus.

A color measurement apparatus that performs color measurement on a printout according to a second aspect of the invention includes a color measurement unit that can perform color measurement on a target by changing a light-receiving angle, and a controller that sets the light-receiving angle dn accordance with an index value representing unique luster of the printout and causes the color measurement unit to perform color measurement at the set light-receiving angle.

A color measurement method performed on a printout using a color measurement apparatus according to a third aspect of the invention includes setting a light-receiving angle in accordance with an index value representing unique luster of the printout and causing the color measurement apparatus to perform the color measurement at the set light-receiving angle.

The aspects of the invention thus structured enable an optimum observation angle to be set in accordance with a level of unique luster of a printout. Consequently, various types of processing can be performed on the basis of the color values of the printout acquired at the optimum observation angle.

BRIEF DESCRIPTION OF THE DRAWINGS

The invention will be described with reference to the accompanying drawings, wherein like numbers reference like elements.

FIGS. 1A to 10 are schematic diagrams explaining an overview of the invention.

DESCRIPTION OF EXEMPLARY EMBODIMENTS

Embodiments of the invention are described below.

1. Overview of the Invention

Figure 1A:
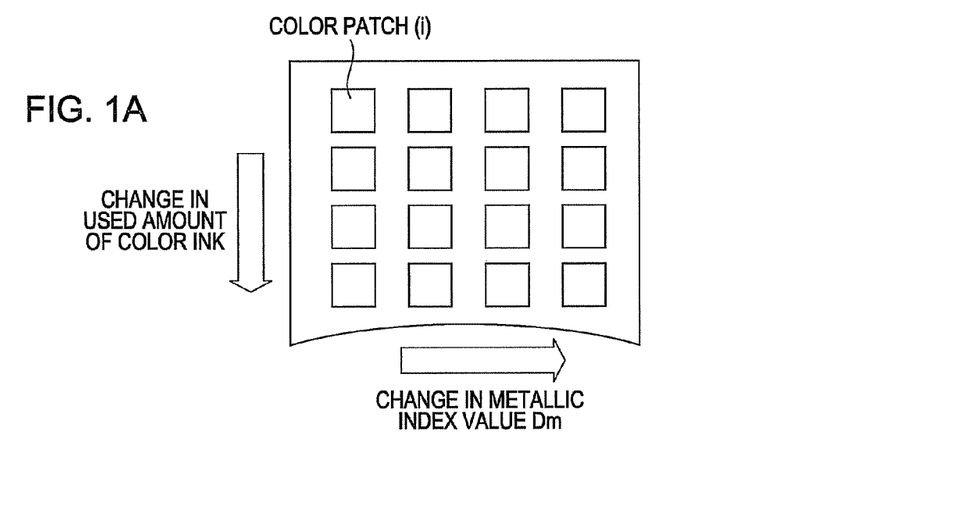
Figure 1B:
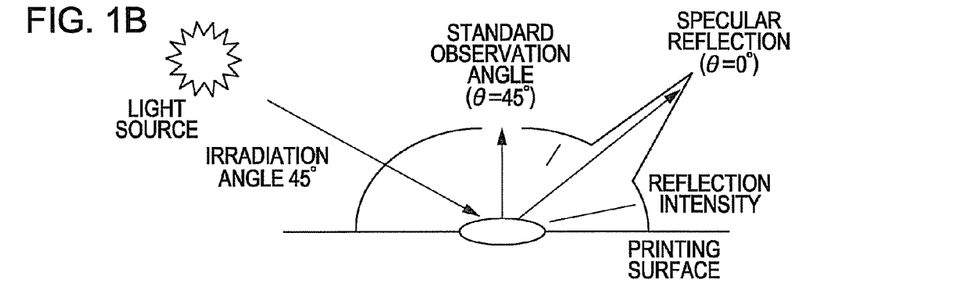
Figure 1C:
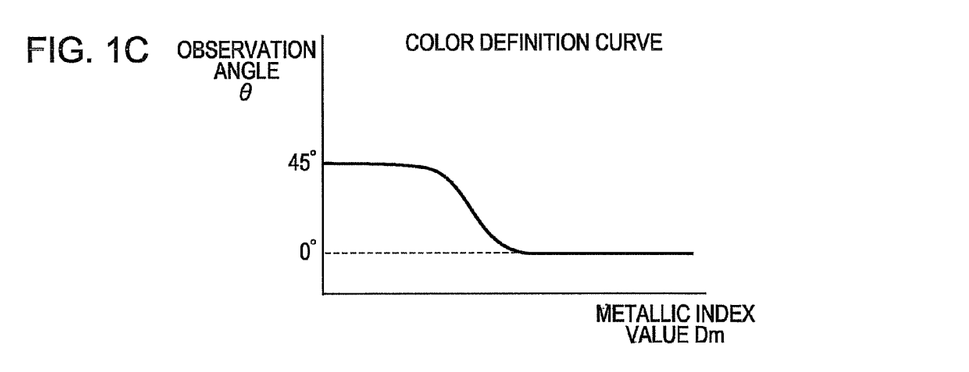

FIGS. 1A to 1C are schematic diagrams explaining an overview of the invention. In the invention, an optimum observation angle is set for amounts of inks including a unique ink that creates metallic luster (hereinafter also described as a metallic ink) on a printout.

The metallic ink is described in detail below. The metallic ink is an ink that causes printouts to exhibit metallic luster. Examples of the metallic ink include an oil-based ink composition that contains a metallic pigment, an organic solvent, and a resin. To cause the metallic ink to effectively create the metallic luster visually, the metallic pigment is preferably composed of plate-shaped particles. In addition, assuming that the plate-shaped particles have a major diameter of X and a minor diameter of Y in the plane thereof and a thickness of Z, the 50% average particle diameter R50 of the circular equivalent diameter obtained from the area of the X-Y plane is preferably 0.5 to 3 μm, and the relationship of R50/z>5 is preferably satisfied. Such a metallic pigment can be formed of an aluminum or aluminum alloy, for example. The density of the metallic pigment contained in the metallic ink may be 0.1 to 10.0% by weight, for example. The composition of the metallic ink is not limited to such a composition. Any composition that can create metal luster can be adopted.

The color value of each among patches formed by changing a used amount of the metallic ink, changes in accordance with the observation angle. The change is described with reference to a color chart illustrated in FIG. 1A, which is a color value diagram, as an example. The color chart is formed by changing used amounts (tone values) of respective inks of a set of ink amounts of the inks including the metallic ink. In the color chart, the patch group of the first column on the left end in FIG. 1A forms gradations as a result of the respective tone values of the inks including no metallic ink being changed. On the abscissa, a level of the metallic luster is changed by changing the used amount of the metallic ink for each patch of the first row. Among the patches thus formed, preferable observation angles change for the patches excluding the patches of the first column when the metallic luster changes. With the change in preferable observation angle, the color values change. This is because spectral reflectance (reflection intensity) of the metallic ink changes at respective reflection angles θ as illustrated in FIG. 1B, and the different reflection angles θ cause the change in color values.

In the invention, the level of metallic luster of a printout is indexed as a metallic index value Dm. The metallic index value Dm is based on glossiness obtained by measuring a printout using a gloss meter. The glossiness corresponds to luminance or brightness L* of the color values at a specular reflection angle with respect to a light source position. For example, in the color chart illustrated in FIG. 1A, as a patch column proceeds from the left to the right in FIG. 1A, the metallic index value Dm changes. If a brightness value L* is acquired as the metallic index value Dm, color values (L*a*b* values) can be used without any change.

In the invention, an optimum observation angle is set in accordance with a level of metallic luster (the metallic index value Dm) of a printout and color values measured at the set observation angle are used as the color values of corresponding amounts of the inks. As illustrated in FIG. 1C, an observation angle θ corresponding to the metallic index value Dm is defined using a color definition curve, for example. In FIG. 1C, the abscissa axis represents the metallic index value Dm while the ordinate axis represents the observation angle θ. The color definition curve illustrated in FIG. 1C defines a correspondence relationship between the metallic index value Dm and the observation angle θ.

Specifically, in the color definition curve illustrated in FIG. 1C, the observation angle θ is set in the vicinity of a standard printout observation angle (θ=45°) when the metallic index value Dm is small while the observation angle θ is set in the vicinity of the specular reflection (θ=0°) when the metallic index value Dm is large. In the following embodiments, the angle of reflection light is 45° when the reflection light is perpendicular to a print surface of a color measurement target while the angle of reflection light is −45° when the reflection light is parallel to the print surface of the measurement target as illustrated in FIG. 1B. Such a relationship between the metallic index value Dm and the observation angle θ can be calculated using the following expression (1), for example, $$Y = \frac{45}{1+c}\left\{\frac{1}{1+\exp\{a \times (X-b)\}} + c\right\} \quad (1)$$

where X is the metallic index value Dm, Y is the observation angle θm, and a, b, and c are parameter values (constants).

The color definition curve is calculated on the basis of subjective values chosen by subjects. Specifically, subjects observe each patch in the color chart illustrated in FIG. 1A at multiple angles. The statistics on the observation angles at which the subjects feel the metallic luster of the patch indicating a certain metallic index value Dm is the most brilliant are collected for all of the patches. Thereafter, the color definition curve is made on the basis of the obtained statistics. The use of the color definition curve enables the color values to be defined at the optimum observation angle in the printout having metallic luster.

The embodiments using the corresponding relationship between metallic index value Dm and the observation angle θ are described below.

2. First Embodiment

2A. Structure of Printing Apparatus

Figure 2:
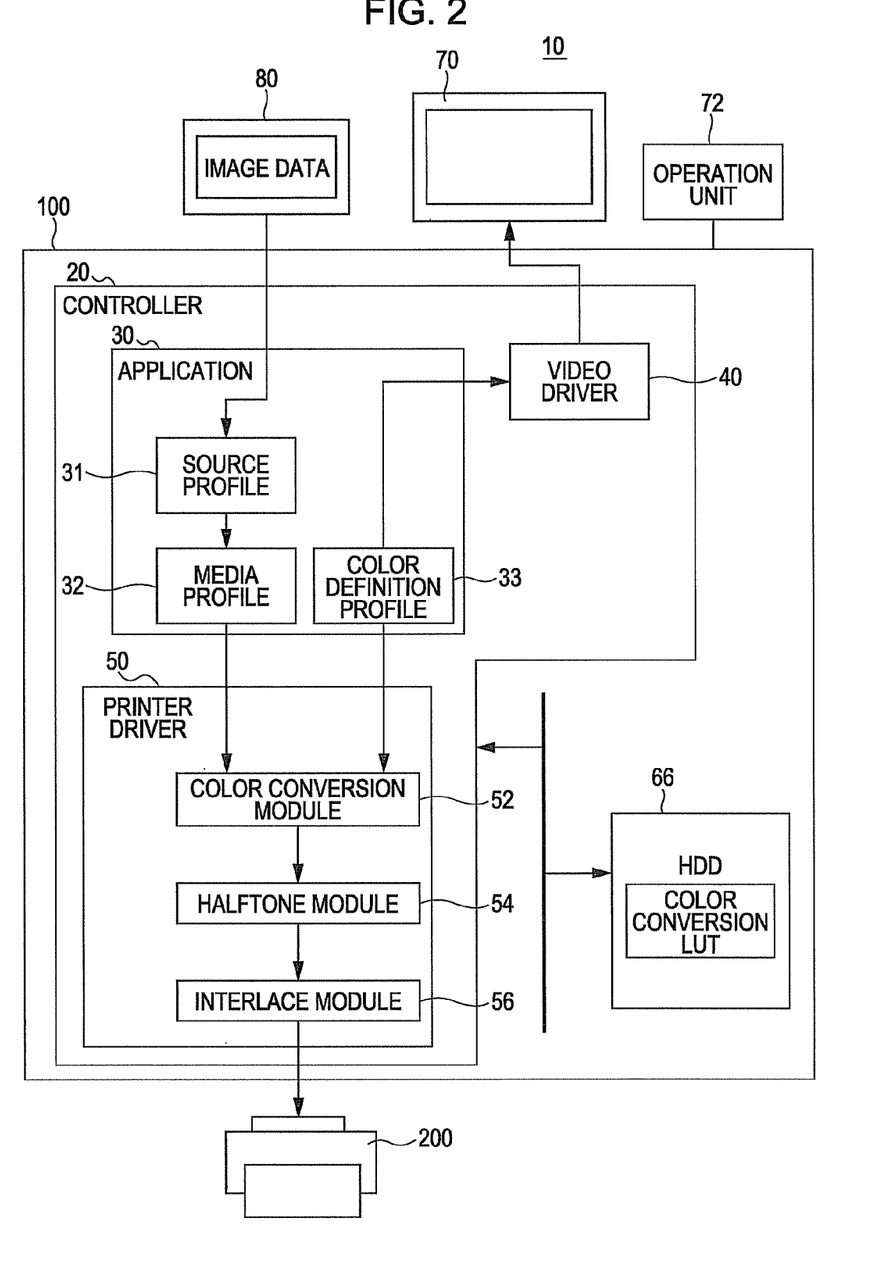
FIG. 2 is a schematic structural view of a printing apparatus.
Figure 3:
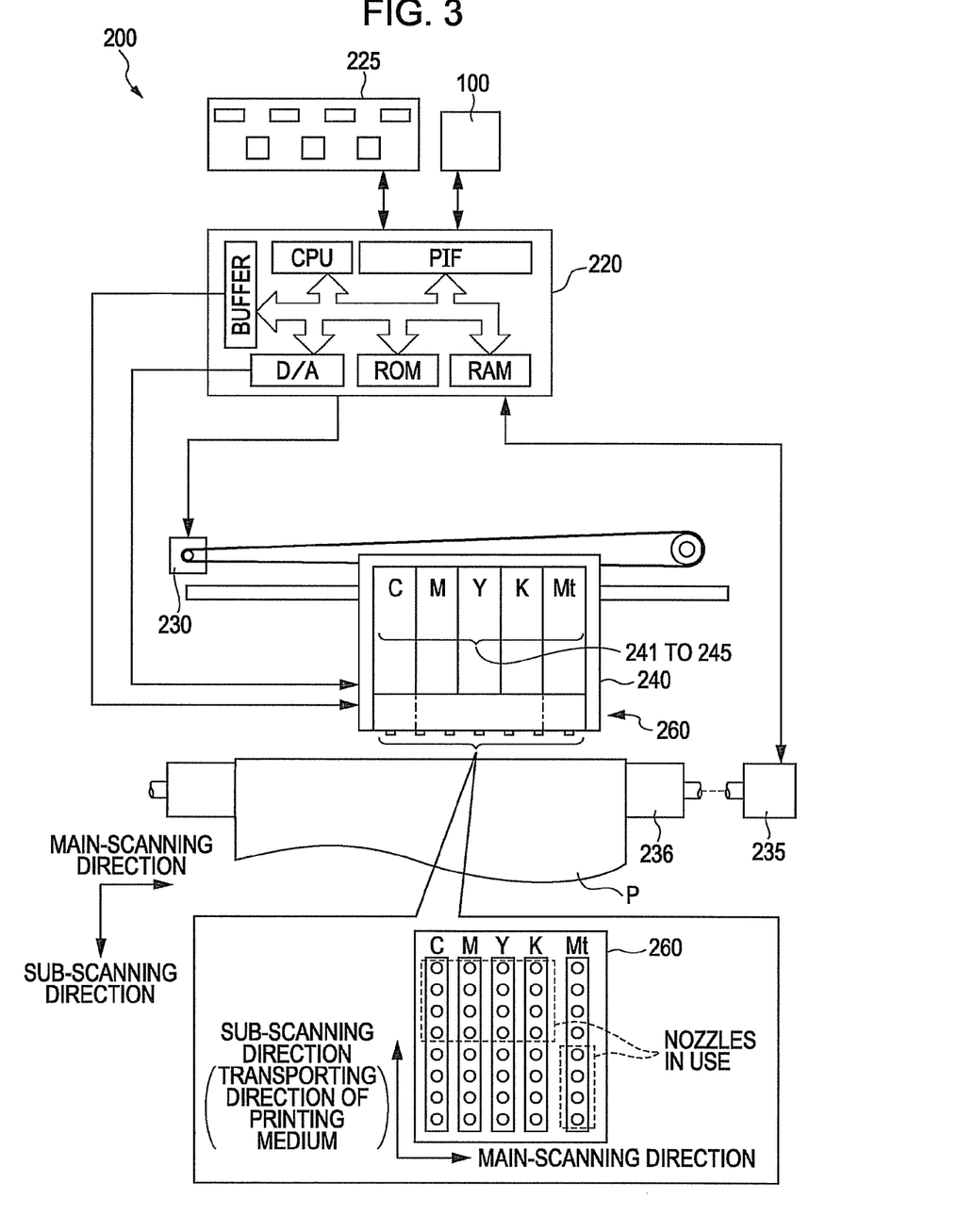
FIG. 3 illustrates an outline of the structure of the printing apparatus.

FIG. 2 is a schematic structural view of a printing apparatus 10. FIG. 3 illustrates an outline of the printing apparatus 10. In a first embodiment, the invention is realized by the printing apparatus 10 including a computer 100 serving as a print control device and a printer 200 that prints images under the control of the computer 100. The printing apparatus 10 functions as a whole as a printing apparatus in the broad sense.

The computer 100 includes a controller 20 and a hard disk drive 66. The controller 20 includes a central processing unit (CPU), a read only memory (ROM), and a random access memory (RAM) and can perform arithmetic operations in accordance with a predetermined program, for example. The computer 100 is connected with cables to a display 70 and an operation unit 72 composed of a keyboard and a mouse. A predetermined operating system is installed in the computer 100. An application program 30, a video driver 40, and a printer driver 50 operate under the operating system. The controller 20 reads the programs from the ROM and the HDD 66 and executes them, thereby achieving the functions of the respective programs.

The application program 30 is used for reproducing image data ORG acquired from a memory card serving as a data supplier 80 and for receiving designation of the metallic index value Dm from a user. In image data of each pixel included in the image data ORG, the color of the pixel is recorded using preliminarily defined color values in terms of metallic luster (hereinafter also described as metallic color values Cm) and using the metallic index value Dm. The metallic color values Cm are recorded using tone values of red (R), green (G), and blue (B) while the metallic index value Dm is recorded as a scalar value. The details of the image data ORG are described later.

The printer driver 50 includes a color conversion module 52, a halftone module 54, and an interlace module 56. The color conversion module 52 converts color component values (R,G,B,Dm) of pixel data of the image data ORG acquired from the application program 30 into a combination of amounts of color inks available in the printer 200 (hereinafter also described as an ink amount set) using a color conversion look-up table (also described as a color conversion LUT). The color conversion LUT is described later.

The halftone module 54 performs processing to produce dot data (hereinafter also described as halftone processing) by performing binarization on the ink amount set after the color conversion. Specifically, the halftone module 54 produces the dot data expressing the image data as existence/absence of the dots using a dither matrix preliminarily prepared by the printer driver 50. The interlace module 56 sorts the produced dot data into the order in which the data is to be transmitted to the printer 200 and outputs the resulting data and also various commands such as a print start command and a print end command to the printer 200.

The structure of the printer 200 is described below. As illustrated in FIG. 3, the printer 200 includes a control circuit 220 that controls the whole of the printer and receives print data from the computer 100, and an operation panel 225. In addition, the printer 200 includes a paper feeding motor 235, a carriage motor 230, a print head 260, a mechanism through which the paper feeding motor 235 transfers a printing medium P, a mechanism through which the carriage motor 230 reciprocates a carriage 240 in the axial direction of a platen 236, and a mechanism that discharges inks and performs dot formation by driving the print head 260.

The control circuit 220 includes a CPU, a ROM, a RAM, and a peripheral interface (PIF) coupled with each other through a bus, and controls main-scanning operation and sub-scanning operation of the carriage 240 by controlling the operation of the carriage motor 230 and the paper feeding motor 235. Upon receiving the print data output from the computer 100 through the PIF, the control circuit 220 can drive the print head 260 by supplying driving signals corresponding to the print data to the print head 260 in synchronization with the movement of the carriage 240 in the main-scanning or the sub-scanning operation.

Cartridges 241 to 245 are mounted on the carriage 240. The cartridges 241 to 245 contain color inks of respective colors of cyan (C), magenta (M), yellow (Y), and black (K), and a metallic ink (Mt) having metallic luster in this order. The print head 260 under the carriage 240 has five ink discharging heads corresponding to the five types of inks of the respective colors. In the embodiment, the ink cartridges 241 to 245 are arranged in the order of C, M, Y, K, and Mt in the main-scanning direction of the carriage 240, as illustrated in FIG. 2. Each nozzle is provided with a piezoelectric element. The control circuit 220 controls contracting and expanding motion of the piezoelectric element, thereby enabling the printer 200 to form dots of each color.

2B. Printing Processing

Figure 4:
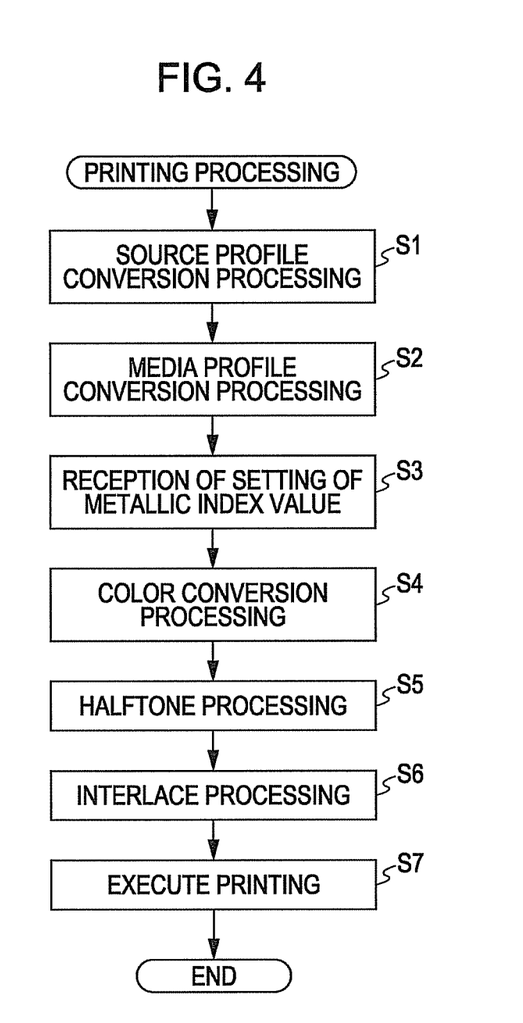
FIG. 4 is a flowchart explaining printing processing.

Printing processing performed by the printing apparatus 10 on the basis of the image data ORG is described below. FIG. 4 is a flowchart explaining the printing processing. The printing processing starts when a user instructs printing in the application program 30. In the invention, the ink amount set is selected using the color conversion LUT in the printing processing. In the embodiment, the color conversion LUT corresponds to a profile.

In step S1 the controller 20 performs conversion processing on the image data ORG using the source profile 31 by using the function of the application program 30. The source profile 31 is a three-dimensional table that converts each color component value of the image data ORG into a preset print standard color. That is, the source profile 31 converts a set of metallic color values (R,G,B) of the color component values (R,G,B,Dm) of the image data ORG into a set of (L*,a*,b*) values.

In step S2, the controller 20 performs conversion processing on the image data ORG after the conversion in step S1 using the media profile 32 by using the function of the application program 30. The media profile 32 is a three-dimensional table used for reproducing the color of a print target image on a predetermined printing medium from the color component values of the image data ORG. That is, the media profile 32 changes a set of (L*,a*,b*) values of the color component values (L*,a*,b*,Dm) of the image data ORG converted using the source profile 31 to a set of color component values (R,G,B).

Figure 5:
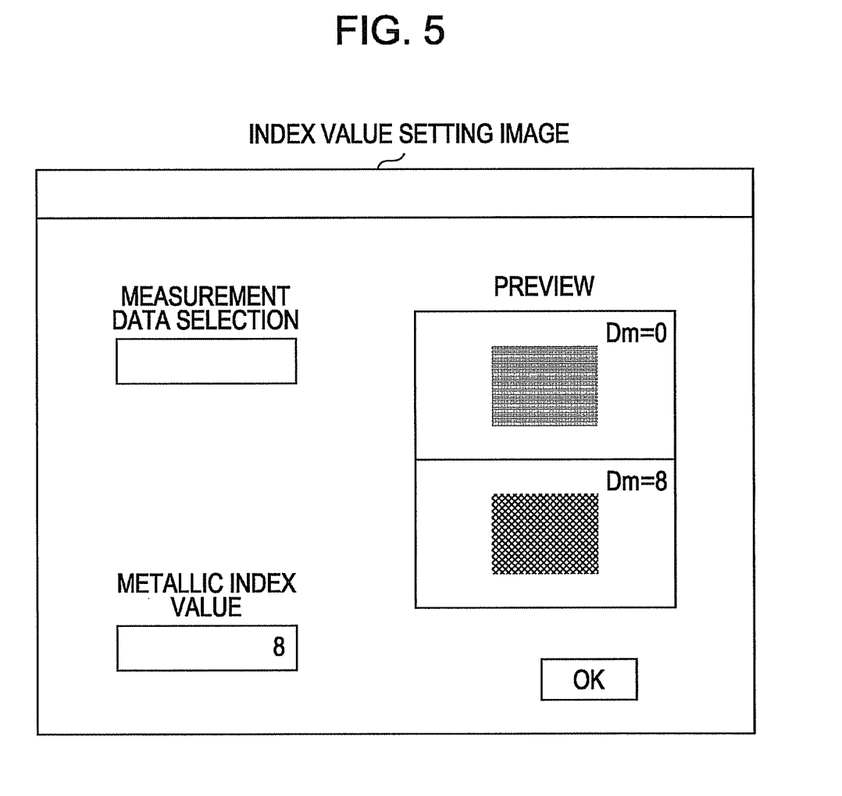
FIG. 5 is a schematic diagram illustrating an example of an index value setting image displayed when a metallic index value is received.

In step S3, the controller 20 receives a setting of the metallic index value Dm. FIG. 5 is a schematic diagram illustrating an example of an index value setting image displayed when the metallic index value Dm is received. The level of metallic luster of a printout (i.e., the metallic index value Dm) is set on the basis of the index value setting image. In the index value setting image, measurement data indicating types of ink amount sets including a metallic ink, the metallic index value Dm, and a preview screen are displayed. A user can change the measurement data and the metallic index value Dm to any settings.

On the preview screen, a preview image when the metallic index value Dm=0 (an ink amount set when the metallic ink Mt is not used) and another preview image for a metallic index value Dm of a certain value set by a user are displayed. The video driver 40 causes the display 70 to display the preview screen so as to reproduce the color values corresponding to the metallic index value Dm. Hereinafter, the observation angle corresponding to the metallic index value Dm is described as θm. For example, the controller 20 selects the observation angle θ corresponding to the designated metallic index value Dm with reference to the color definition profile 33 that records the correspondence relationship between the metallic index value Dm and the observation angle θ in accordance with the color definition curve (FIG. 1C). The video driver 40 determines the color values acquired when the color values are measured at the selected observation angle θ, converts the color values into the RGB values, and produces the preview image.

As the metallic index value Dm increases, values of the color values (particularly, brightness L*) may exceed a reproduction color gamut of the display 70. In such a case, the color values may be reproduced within a reproducible color gamut of the display 70 because the color values corresponding to the metallic index value Dm cannot be exactly reproduced.

In step S4, the controller 20 performs the color conversion processing using the color conversion LUT by using the function of the printer driver 50. In the color conversion LUT used at this step, an ink amount set is associated with the metallic index value Dm designated in step S3. For example, when the metallic index value Dm=8, the color conversion LUT is used that causes the printer 200 to select the ink amount set corresponding to the metallic index value Dm=8.

In step S5, the controller 20 performs the halftone processing on the ink amount data after the color conversion performed by the function of the halftone module 54. In step S6, the controller 20 performs the interlace processing on the ink amount data after the halftone processing by using the function of the interlace module 56.

In step S7, the ink amount data after subjected to the interlace processing is output to the printer 200, and the printer 200 performs printing.

2C. Forming of Printing Apparatus

Figure 6:
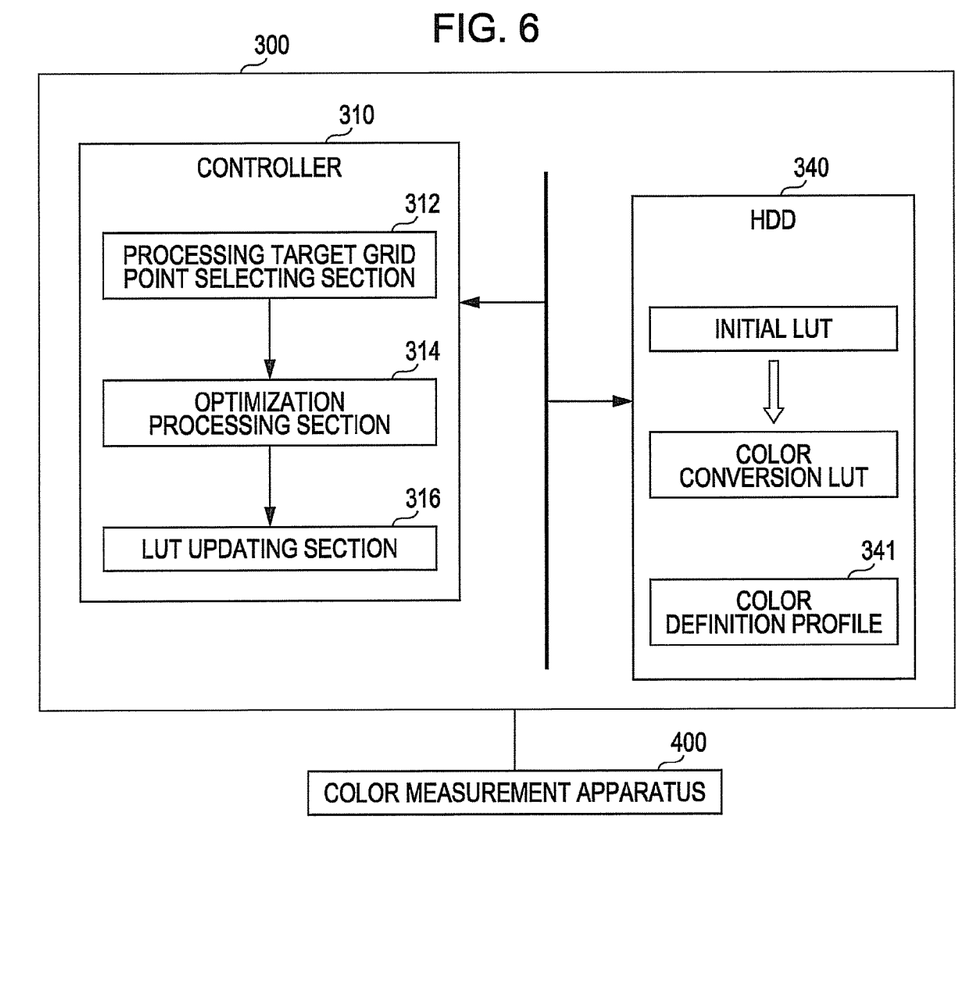
FIG. 6 is a block diagram illustrating a color conversion look-up table (LUT) creation apparatus.
Figure 7:
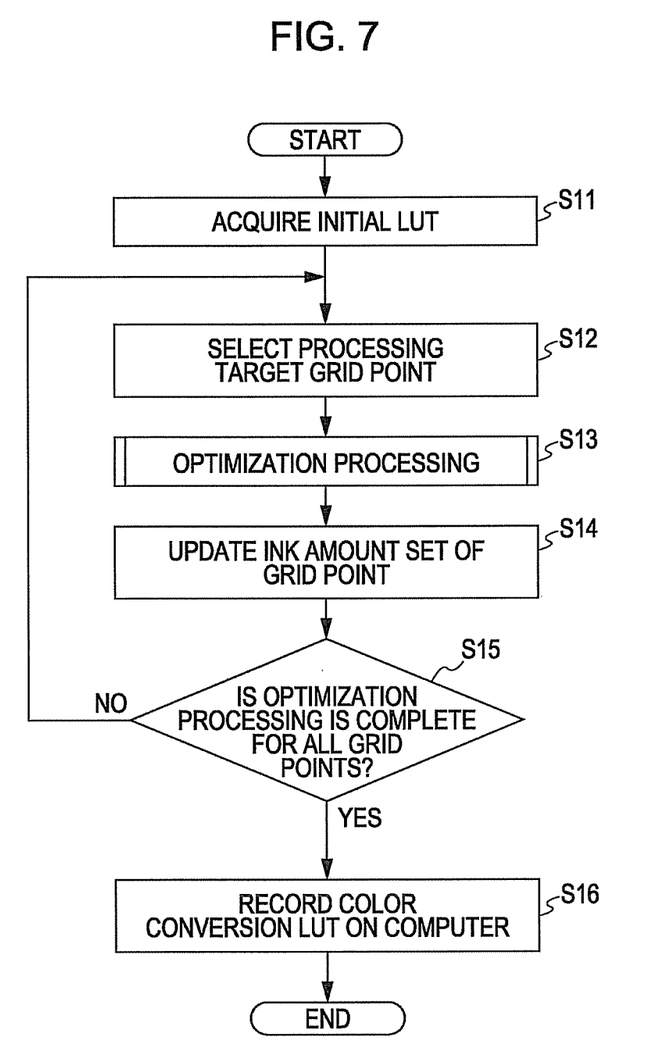
FIG. 7 is a flowchart of forming of the printing apparatus.

A method for forming the printing apparatus 10 is described below. Particularly, the creation of the color conversion LUT used by the printer 200 is mainly described. FIG. 6 is a block diagram illustrating a color conversion LUT creation apparatus. FIG. 7 is a flowchart of forming of the printing apparatus 10.

A color conversion LUT creation apparatus 300 is achieved by a computer including a controller 310 provided with a CPU, a ROM, and a RAM, a hard disk drive 340, a monitor (not illustrated), and various input interfaces (not illustrated). The color conversion LUT creation apparatus 300 can acquire colorimetric data output from a color measurement apparatus 400 as a result of being connected to the color measurement apparatus 400. The controller 310 achieves the respective functions of a processing target grid point selecting section 312, an optimization processing section 314, and an LUT updating section 316 by executing programs recorded on the ROM (not illustrated).

A method of forming the printing apparatus 10 is described below with reference to FIG. 7.

First, the controller 310 acquires an initial LUT (step S11). The initial LUT is a table in which the color component values (R,G,B,Dm) including the metallic index value Dm and the metallic color values Cm (R,G,B) are associated with respective output values of the ink amount set (C,M,Y,K,Mt). Hereinafter, an input value specified by the color component values (R,G,B,Dm) is also described as a grid point. All of the tone values of the metallic color values Cm are not recorded, but only typical values of them are recorded as the input value recorded in the initial LUT.

Then, the controller 310 selects a processing target grid point from the initial LUT by using the function of the processing target grid point selecting section 312 (step S12). The controller 310 performs the optimization processing, by using the function of the optimization processing section 314, on the ink amount set (C,M,Y,K,Mt) set for the selected grid point (step S13). In the optimization processing, the ink amount set (C,M,Y,K,Mt) corresponding to the grid point of the initial LUT is updated such that the ink amount set satisfies the metallic color values Cm determined in accordance with the metallic index value.

The controller 310 updates the initial LUT by overwriting the ink amount set with the updated ink amount set on the target grid point of the initial LUT using the function of the LUT updating section 316 (step S14). If the updating of the ink amount set is not complete for all of the grid points (No in step S15), the processing is repeated from step S12 to step S14 until the updating is complete for all of the grid points. Then, the controller 310 records the initial LUT after the updating in a recording unit (the hard disk drive 66) of a computer (e.g., the computer 100 illustrated in FIG. 2) as a color conversion LUT (step S16, which is a third process). The processing illustrated in FIG. 7 is repeated until the color conversion LUTs corresponding to all of the metallic index values Dm selectable in the index value setting image are created.

2D. Optimization Processing

Figure 8:
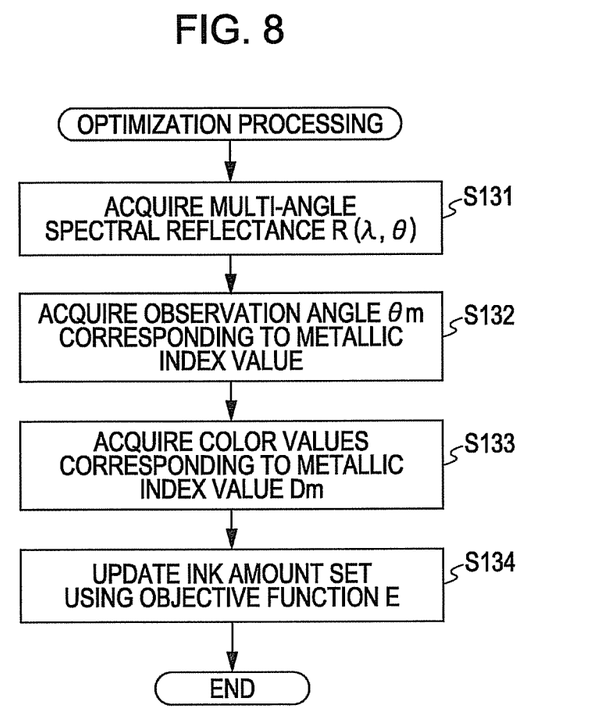
FIG. 8 is a flowchart explaining optimization processing.
Figure 9A:
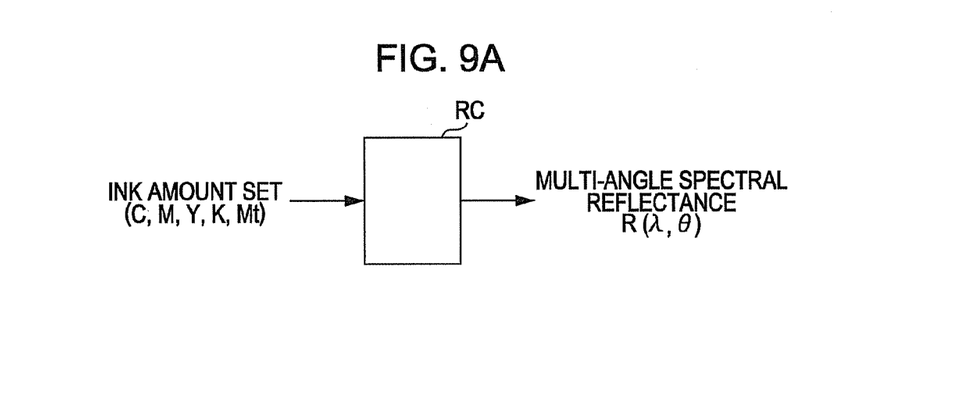
FIGS. 9A and 9B are explanatory views of a multi-angle spectral reflectance printing model converter.
Figure 9B:
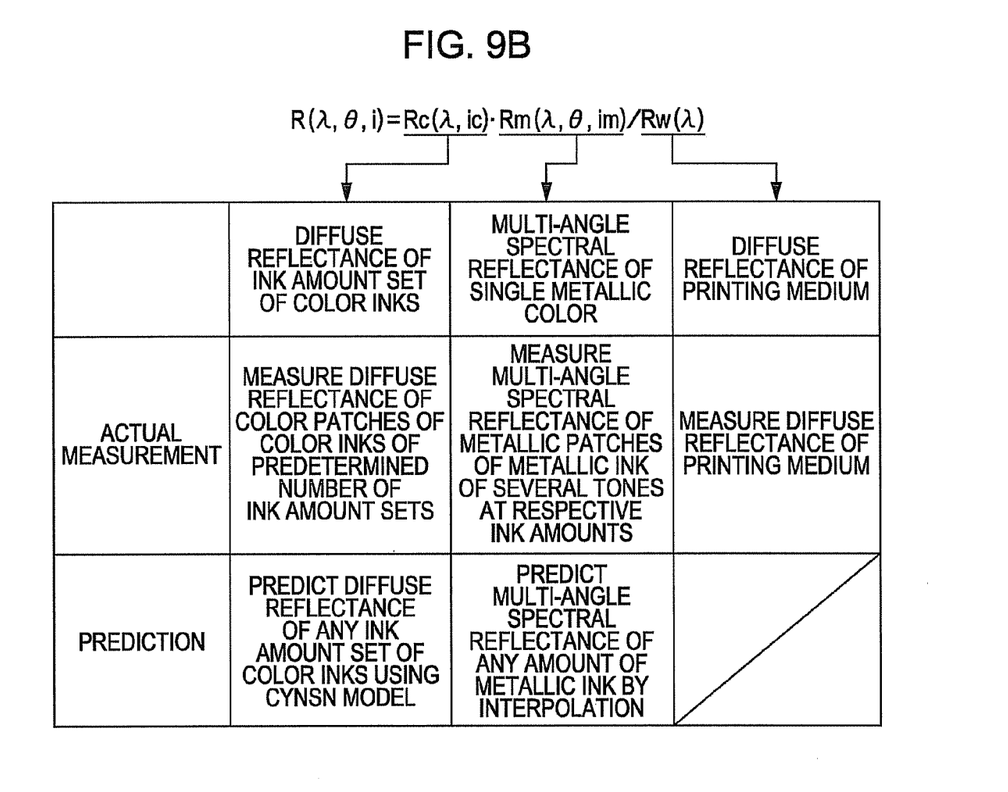
Figure 10:
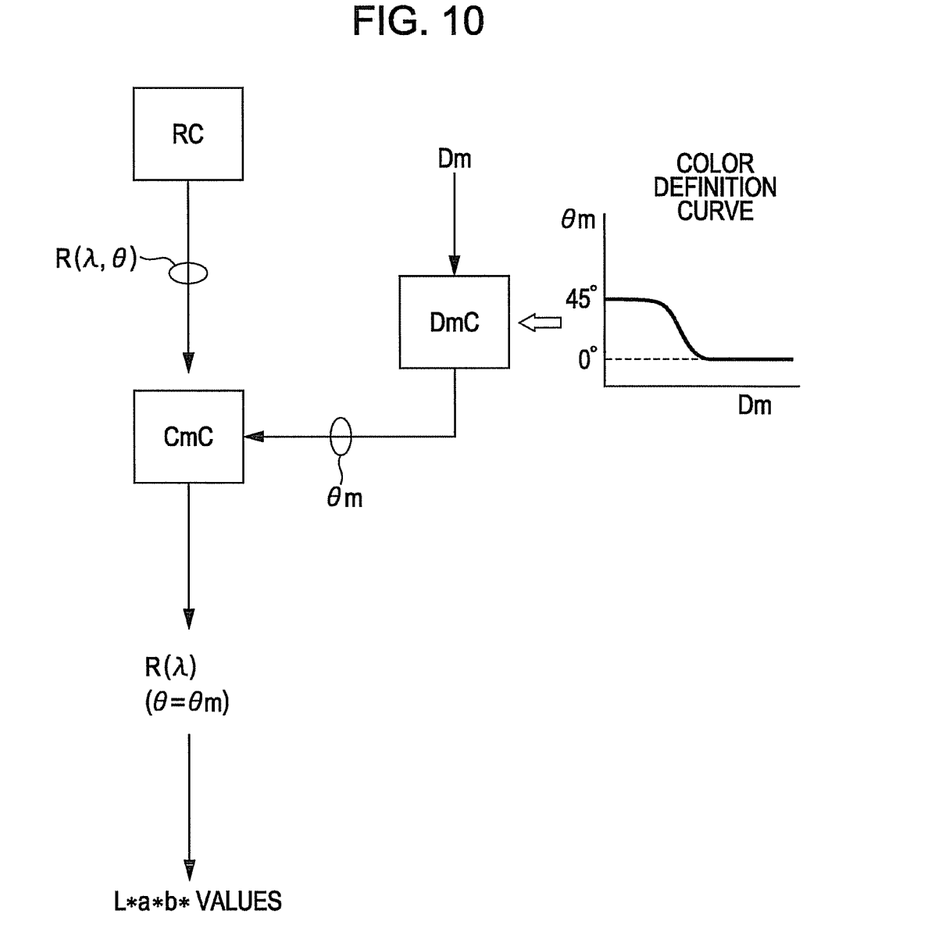
FIG. 10 is an explanatory view of converters.

The optimization processing performed in step S13 in FIG. 7 is described below. FIG. 8 is a flowchart explaining the optimization processing. FIGS. 9A and 9B are explanatory views of a multi-angle spectral reflectance printing model converter RC. FIG. 10 is an explanatory view of converters CmC and DmC.

In step S131 of FIG. 8, the optimization processing section 314 acquires a multi-angle spectral reflectance R ($\lambda$,$\theta$) of the ink amount set using the multi-angle spectral reflectance printing model converter RC. As illustrated in FIG. 9A, the multi-angle spectral reflectance printing model converter RC converts any ink amount set (C,M,Y,K,Mt) into a multi-angle spectral reflectance R ($\lambda$,$\theta$). The spectral reflectance R ($\lambda$,$\theta$) at a predetermined observation angle $\theta$m ($\theta$m: 0° to 180°) of any ink amount set (C,M,Y,K,Mt) can be acquired by the multi-angle spectral reflectance printing model converter RC. In the embodiment, the multi-angle spectral reflectance R ($\lambda$,$\theta$) is defined by the following expression (2).

$$R(\lambda,\theta,i)=Rc(\lambda,ic)\cdot Rm(\lambda,\theta,im)/Rw \quad (2)$$

where $\lambda$ is a wavelength element of reflection light, $\theta$ is a reflection angle element of reflection light, i is the ink amounts (C,M,Y,K,Mt), ic is the ink amount set of color inks (C,M,Y,K), and im is the ink amount of the metallic ink (Mt).

In expression (2), Rc ($\lambda$,ic) represents the spectral reflectance (diffusion reflectance: an incident angle $\theta$ of incident light is 45 degrees and a reflection angle $\theta$ is zero degrees) of a print image of color inks (C,M,Y,K) of an ink amount set ic excluding the metallic ink Mt. Rm ($\lambda$,$\theta$,im) represents the multi-angle spectral reflectance of a print image of the metallic ink of the ink amount im alone. Rw ($\lambda$) represents the spectral reflectance (diffusion reflectance) of a background color of a predetermined printing medium, i.e., a printing medium used for the printing processing.

As illustrated in FIG. 9B, the multi-angle spectral reflectance printing model converter RC predicts the multi-angle spectral reflectance R ($\lambda$,$\theta$) of any ink amount set (C,M,Y,K, Mt) from the actual measurement values (colorimetric values) of Rc ($\lambda$,$\theta$) and Rm ($\lambda$,im) of the predetermined number of ink amount sets (C,M,Y,K,Mt).

A method of predicting the spectral reflectance Rc ($\lambda$,ic) of color inks used by the multi-angle spectral reflectance printing model converter RC is described below. The color patches (i) are printed on the basis of a plurality of representative points in an ink amount space of the color inks (C,M,Y,K) and the diffusion spectral reflectance of the color patches is measured by a color measurement apparatus. The diffusion spectral reflectance Rc ($\lambda$,ic) when printing is performed using any color ink is predicted using a cellular Yule-Nielsen spectral Neugebauer (CYNSN) model and the obtained database of diffusion spectral reflectance. The cellular Yule-Nielsen spectral Neugebauer model is a known technique (e.g., that described in JP-T-2007-511161) and the description thereof is thus omitted.

A method of predicting the multi-angle spectral reflectance Rm ($\lambda$,$\theta$,im) of the metallic ink (Mt) is described below. Print images of the metallic ink (hereinafter also described as metallic patches) are printed with respective ink amounts by changing the ink amount step-by-step. The multi-angle spectral reflectance the printed metallic patches is measured by a spectral reflectometer. The multi-angle spectral reflectance Rm ($\lambda$,$\theta$,im) when printing is performed at any ink amount of the metallic ink is predicted by interpolating using the database of the multi-angle spectral reflectance at the respective ink amounts of the metallic ink obtained by the measurement.

Rw ($\lambda$) is acquired by measuring the printing medium with the spectral reflectometer. The multi-angle spectral reflectance printing model converter RC acquires the multi-angle spectral reflectance R ($\lambda$,$\theta$,i) by performing an arithmetic operation using expression (1) on the basis of the spectral reflectance Rc ($\lambda$,ic) of color inks (C,M,Y,K), the multi-angle spectral reflectance Rm ($\lambda$,$\theta$,im) of the metallic ink (Mt), and the Rw ($\lambda$) of the background color thus obtained.

In step S132 in FIG. 8, the optimization processing section 314 acquires the optimum observation angle $\theta$m corresponding to the metallic index value Dm using the metallic index value converter DmC. As illustrated in FIG. 10, the metallic index value converter DmC acquires the optimum observation angle $\theta$m of the ink amount set with respect to any metallic index value. Specifically, the metallic index value converter DmC acquires the observation angle $\theta$m with respect to the metallic index value Dm on the basis of the color definition profile 341. In the color definition profile 341, the correspondence relationship between the metallic index value Dm and the observation angle $\theta$m is recorded on the basis of the color definition curve represented by expression (1). In this way, a first process of the invention is achieved by the processing in step S132.

In step S133 in FIG. 8, the optimization processing section 314 acquires the color values corresponding to the metallic index value Dm using the metallic color value converter CmC. As illustrated in FIG. 10, the metallic color value converter CmC acquires the multi-angle spectral reflectance R ($\lambda$,$\theta$m,ic) corresponding to the observation angle $\theta$m acquired by the metallic index value converter DmC from the multi-angle spectral reflectance R ($\lambda$,$\theta$,ic) of any ink amount set acquired by the multi-angle spectral reflectance printing model converter RC. Then, L*a*b*values are acquired from the R (λ,θm,ic) acquired by the metallic color value converter CmC using a known conversion formula. Accordingly, the acquired metallic color values Cm are the color values corresponding to the metallic index value Dm.

The observation angle θm acquired by the metallic index value converter DmC may not be included in the angle θ of the multi-angle spectral reflectance R (λ,θ,ic). In such a case, the multi-angle spectral reflectance R (λ,θm,ic) corresponding to the observation angle θ m is acquired by interpolating the angle θ of the multi-angle spectral reflectance R (λ,θ,ic).

In step S134, the optimization processing section 314 updates the ink amount set using an objective function E. The optimization processing section 314 calculates an evaluation function E represented by the following expression (3) on the basis of the metallic index values Cm acquired by the respective converters.

$$E = w1 \langle Cm0 \rangle - \langle Cmx \rangle \tag{3}$$

In expression (3), w1 represents a predetermined weight coefficient and < > indicates a vector. Cm0 represents L*a*b*values of the values (R,G,B) of the processing target grid point (R,G,B,Mt). The values are acquired using the source profile 31, for example. The optimization processing section 314 calculates the evaluation function E represented by expression (3) for each grid point and continues to update the ink amount set until the evaluation function E reaches a minimum.

As a result of the processing performed by the optimization processing section 314, the ink amount set (C,M,Y,K,Mt) satisfying the metallic color value Cm at a predetermined observation angle θm is set for all of the grid points. As a result, the color conversion LUTs corresponding to the respective metallic index values Dm are created. In this way, a second step of the invention is achieved by the processing in step S133 and step S134.

As described above, in the first embodiment, the color values at the optimum observation angle are acquired in accordance with unique luster of a printout designated by a user. In addition, a printing apparatus can be provided that can reproduce the color values corresponding to the unique luster.

2. Second Embodiment

Figure 11:
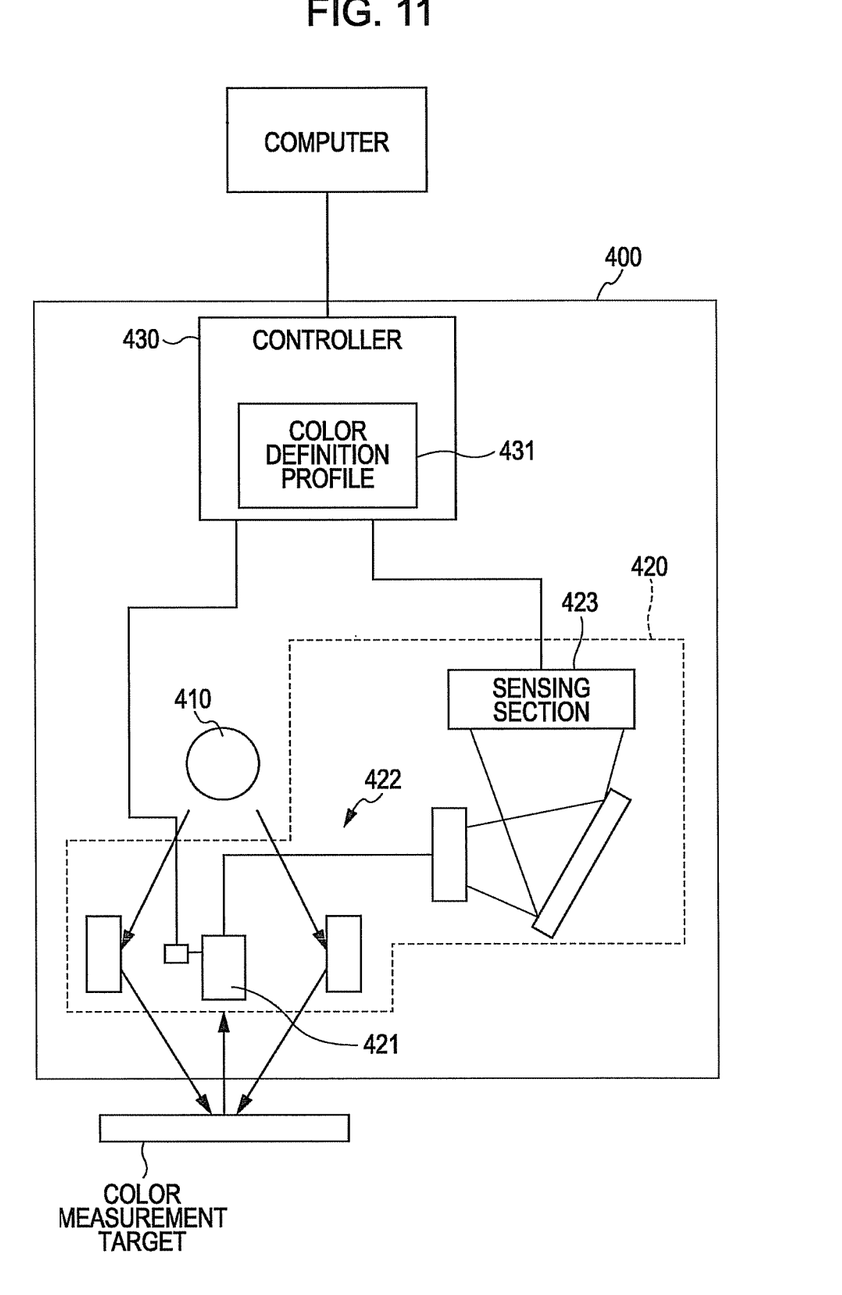
FIG. 11 is a schematic diagram explaining a structure of a color measurement apparatus.
Figure 12:
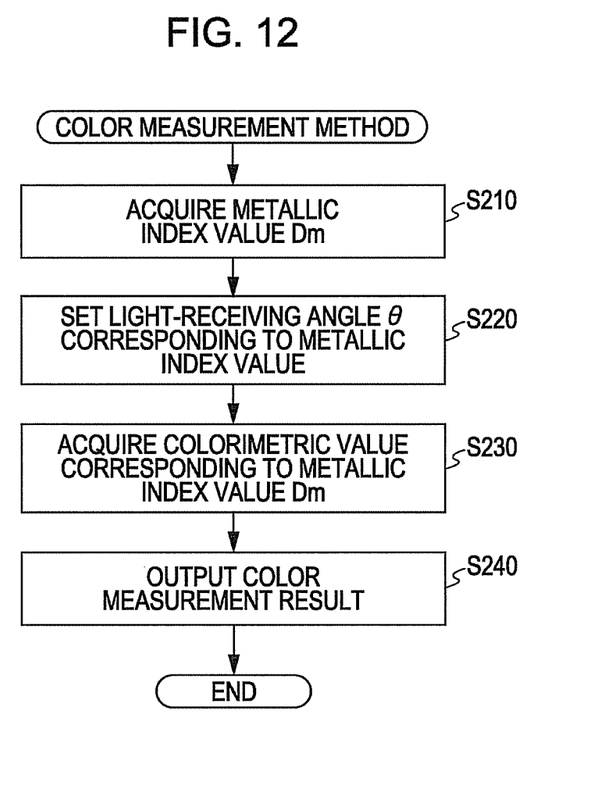
FIG. 12 is a flowchart explaining a color measurement method performed by the color measurement apparatus.

In a second embodiment, a color measurement apparatus to which the concept of the invention is applied is described as an example. FIG. 11 is a schematic diagram explaining a structure of a color measurement apparatus 400. FIG. 12 is a flowchart explaining a color measurement method performed by the color measurement apparatus 400.

The color measurement apparatus 400 can perform color measurement on printouts such as color charts and output the measurement results to a computer. The color measurement apparatus 400 can change a light-receiving angle in multiple steps so as to acquire the optimum color values corresponding to a level of metallic luster. In order to achieve the above, the color measurement apparatus 400 includes a light source 410, a color measurement unit 420, and a controller 430.

The color measurement unit 420 includes a light-receiving section 421 that receives light reflected by a color measurement target, an optical system 422 that guides light received by the light-receiving section 421, and a sensing section 423 that detects intensity of the guided light. The light-receiving section 421 is provided with a motor that changes a light-receiving angle (observation angle) θm relative to the color measurement target and can change the light-receiving angle θm in multiple steps by driving the motor. The sensing section 423 can measure intensity (also described as reflectance) of light in a wavelength range including a visual light range (380 nm to 730 nm) for each predetermined wavelength.

The controller 430 includes a CPU, a ROM, and a RAM. The controller 430 records the color definition profile 431 that specifies the corresponding relationship between the metallic index value Dm and the light-receiving angle (observation angle) θm in the ROM. In the color definition profile 431, the metallic index value Dm and the light-receiving angle θm correspond to each other in accordance with the color definition curve represented by expression (1). In addition, the controller 430 can receive input of the metallic index value Dm through an input section (not illustrated).

A color measurement method for printouts performed by the color measurement apparatus 400 is described below with reference to FIG. 12. In the following description, it is assumed that recording is performed on a printout to be measured by the color measurement apparatus 300 using inks including a metallic ink and a user knows the metallic index value Dm of the printout in advance.

In step S210, the controller 430 receives the metallic index value Dm. For example, the metallic index value Dm input by a user is received on a user interface (UI) screen (not illustrated) displayed on the computer.

In step S220, the controller 430 changes the light-receiving angle θm of the light-receiving section 421 in accordance with the metallic index value Dm received in step S210. That is, the controller 430 acquires the light-receiving angle θm corresponding to the input metallic index value Dm on the basis of the color definition profile 431. Thereafter, the controller 430 changes the light-receiving angle of the light-receiving section 421 on the basis of the acquired light-receiving angle θm.

In step S230, the controller 430 acquires a colorimetric value. The colorimetric value acquired by the controller 430 is a value acquired on the basis of incident light received by the light-receiving section 421 at the light-receiving angle θm designated in accordance with the metallic index value Dm. For example, when the colorimetric value is acquired as the spectral reflectance, the controller 430 converts the spectral reflectance into the color values (L*a*b* values) on the basis of a known conversion formula.

In step S240, the controller 430 outputs the acquired color values to the computer. That is, the color values corresponding to the metallic index value Dm are input to the computer 100.

As described above, in the second embodiment, a color measurement apparatus can be realized that can acquire the color values in accordance with a level of metallic luster. That is, the color measurement apparatus can acquire the color values at the optimum observation angle from printouts having colors that look different depending on the observation angle.

The color measurement apparatus 400 may use a method in which color measurement is performed on the color measurement target by changing the light-receiving angle to multiple angles and thereafter the controller 430 selects only the colorimetric value corresponding to the metallic index value Dm and outputs the selected colorimetric value to the computer, besides the method in which color measurement is performed by changing the light-receiving angle θm in accordance with the metallic index value Dm.

It is needless to say that the invention is not limited to the embodiments described above. That is, changing of the combinations of the replaceable members and the structures described in the embodiments, replacement of the members and structures described in the embodiments with those of known techniques replaceable with those described in the embodiments and changing the combinations thereof, and replacement of the members and structures described in the embodiments with those that persons skilled in the art can readily assume as a substitute for those described in the embodiments and changing of the combinations thereof are included in embodiments of the invention.

What is claimed is:

1. A color measurement apparatus that performs color measurement on a printout, the apparatus comprising:
   a color measurement unit that is capable of performing color measurement on a target by changing a light-receiving angle; and
   a controller that causes the color measuring unit to perform color measurement at the light-receiving angle corresponding to an index value representing unique luster of the printout.

2. The color measurement apparatus according to claim 1, wherein as the index value increases the light-receiving angle approaches the light-receiving angle at which specular reflection occurs.

3. The color measurement apparatus according to claim 1, wherein the index value is glossiness of a metallic ink.

4. A printing apparatus, comprising the color measurement apparatus according to claim 1.

5. A color measurement method performed on a printout using a color measurement apparatus, the method comprising:
   setting a light-receiving angle in accordance with an index value representing unique luster of the printout; and
   causing the color measurement apparatus to perform color measurement at the set light-receiving angle.

* * * * *

UNITED STATES PATENT AND TRADEMARK OFFICE
CERTIFICATE OF CORRECTION

| | | |
|---|---|---|
| PATENT NO. | : 8,780,349 B2 | Page 1 of 1 |
| APPLICATION NO. | : 13/745498 | |
| DATED | : July 15, 2014 | |
| INVENTOR(S) | : Yoshio Okumura | |

It is certified that error appears in the above-identified patent and that said Letters Patent is hereby corrected as shown below:

On the Title page, Item (71) Applicant, please replace "Yoshio Okumura, Suwa (JP)" with "Seiko Epson Corporation, Tokyo (JP)".

Signed and Sealed this
Twenty-ninth Day of September, 2015

Michelle K. Lee
*Director of the United States Patent and Trademark Office*